(12) United States Patent
Hafez

(10) Patent No.: US 10,849,636 B2
(45) Date of Patent: Dec. 1, 2020

(54) DEVICE AND METHOD FOR FITTING AN ARTIFICIAL KNEE JOINT USING UNIVERSAL ELECTRONIC TEMPLATES WHICH CAN BE ADAPTED TO ALL ARTIFICIAL JOINTS

(71) Applicant: Mahmoud Alm El Din Hafez, Giza (EG)

(72) Inventor: Mahmoud Alm El Din Hafez, Giza (EG)

( * ) Notice: Subject to any disclaimer, the term of this patent is extended or adjusted under 35 U.S.C. 154(b) by 373 days.

(21) Appl. No.: 14/964,609

(22) Filed: Dec. 10, 2015

(65) Prior Publication Data
US 2016/0174994 A1    Jun. 23, 2016

Related U.S. Application Data

(63) Continuation-in-part of application No. PCT/EG2013/000014, filed on Jun. 11, 2013.

(51) Int. Cl.
*A61B 17/17* (2006.01)
*A61B 17/15* (2006.01)
(Continued)

(52) U.S. Cl.
CPC ........ *A61B 17/1764* (2013.01); *A61B 17/155* (2013.01); *A61B 17/157* (2013.01); *A61B 17/1721* (2013.01); *A61F 2/30942* (2013.01); *A61F 2/38* (2013.01); *A61F 2/461* (2013.01); *A61B 2017/568* (2013.01); *A61B 2034/108* (2016.02); *A61F 2002/4658* (2013.01)

(58) Field of Classification Search
CPC ............ A61B 2034/108; A61B 17/157; A61B 17/155; A61B 2017/568
See application file for complete search history.

(56) References Cited

U.S. PATENT DOCUMENTS

| 8,591,516 B2 | 11/2013 | Metzger et al. |
| 8,668,700 B2 * | 3/2014 | Catanzarite .......... A61B 17/155 606/88 |

(Continued)

FOREIGN PATENT DOCUMENTS

| WO | 2012154407 A2 | 11/2012 |
| WO | 2014198279 A1 | 12/2014 |

OTHER PUBLICATIONS

Hafez MA, Chelule K, Seedhom BB, Sherman KP. Computer-assisted total knee arthroplasty using patient-specific templating. Clinical Orthopaedic and Related Research. 2006;444:184-192.
(Continued)

*Primary Examiner* — David W Bates
(74) *Attorney, Agent, or Firm* — King & Schickli, PLLC

(57) ABSTRACT

This invention is a device and a method for preparing a knee joint for a prosthesis in a patient undergoing TKA surgery for any knee implant (prosthesis). The device and the method are used in a universal and an open platform fashion for any currently available knee implant, all patient specific implants and any knee implants that could be produced in future.
The device is a patient specific instrument, which is based on a method comprising of image based (CT, MRI or computed X-ray) 3-D preoperative planning to design the templates (PSI) that are used to perform the knee surgery for any knee implant in a universal and open platform fashion.

10 Claims, 9 Drawing Sheets

(51) Int. Cl.
*A61B 34/10* (2016.01)
*A61F 2/30* (2006.01)
*A61F 2/38* (2006.01)
*A61F 2/46* (2006.01)
*A61B 17/56* (2006.01)

(56) References Cited

U.S. PATENT DOCUMENTS

| | | | |
|---|---|---|---|
| 2005/0234461 A1* | 10/2005 | Burdulis, Jr. | A61B 17/155 606/79 |
| 2008/0114370 A1* | 5/2008 | Schoenefeld | A61B 17/1721 606/96 |
| 2008/0281329 A1* | 11/2008 | Fitz | A61B 5/4528 606/88 |
| 2009/0157083 A1* | 6/2009 | Park | A61B 17/15 606/88 |
| 2010/0298894 A1* | 11/2010 | Bojarski | A61B 34/10 606/86 R |
| 2011/0071533 A1 | 3/2011 | Metzger et al. | |
| 2011/0218545 A1* | 9/2011 | Catanzarite | A61B 17/155 606/96 |
| 2011/0245835 A1* | 10/2011 | Dodds | A61B 17/1764 606/87 |
| 2012/0290272 A1 | 11/2012 | Bryan | |
| 2013/0191085 A1* | 7/2013 | Li | A61B 17/32053 703/1 |
| 2014/0378979 A1* | 12/2014 | Stone | A61B 17/152 606/88 |
| 2015/0142000 A1* | 5/2015 | Seedhom | A61F 2/38 606/87 |
| 2020/0060766 A1* | 2/2020 | Hafez | A61B 17/56 |
| 2020/0197023 A1* | 6/2020 | Chafez | A61F 2/30942 |

OTHER PUBLICATIONS

Taylor & Francis healthsciences; Abstracts from CAOS International 2004 4th Annual Meeting of the International Society for Computer Assisted Orthopaedic Surgery Chicago, Illinois, Jun. 16-19, 2004.

Hafez, et al.; "Computer-Assisted Knee Surgery: An Overview"; Joint Replacement and its Alternatives; 2005; US.

* cited by examiner

Figure 1: Femoral template
All views ( 1-A, 1-B, 1-C, 1-D, 1-E, 1-F, 1-G, 1-H )
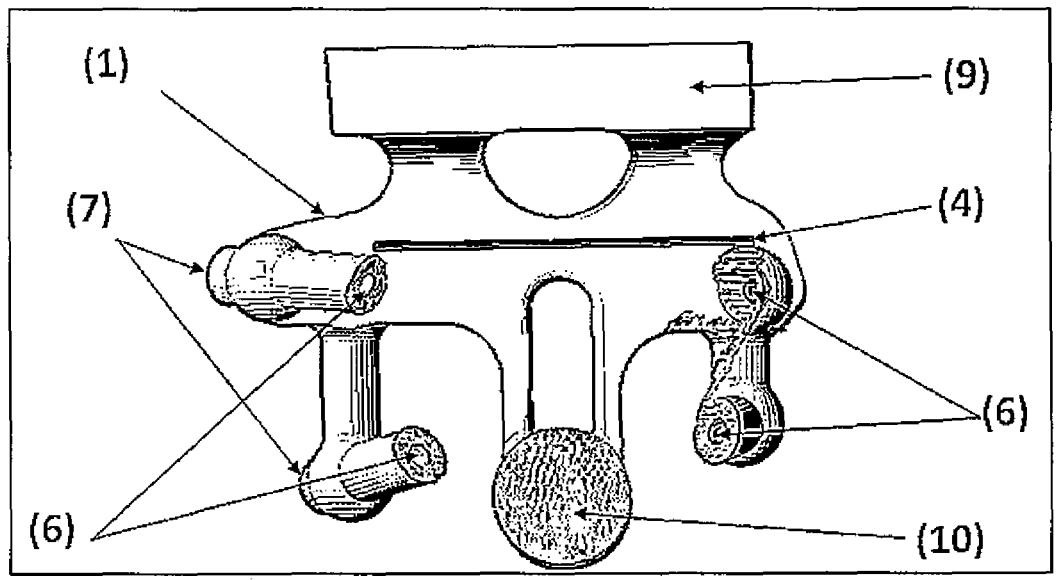
Figure 1-A Femoral template, inside view
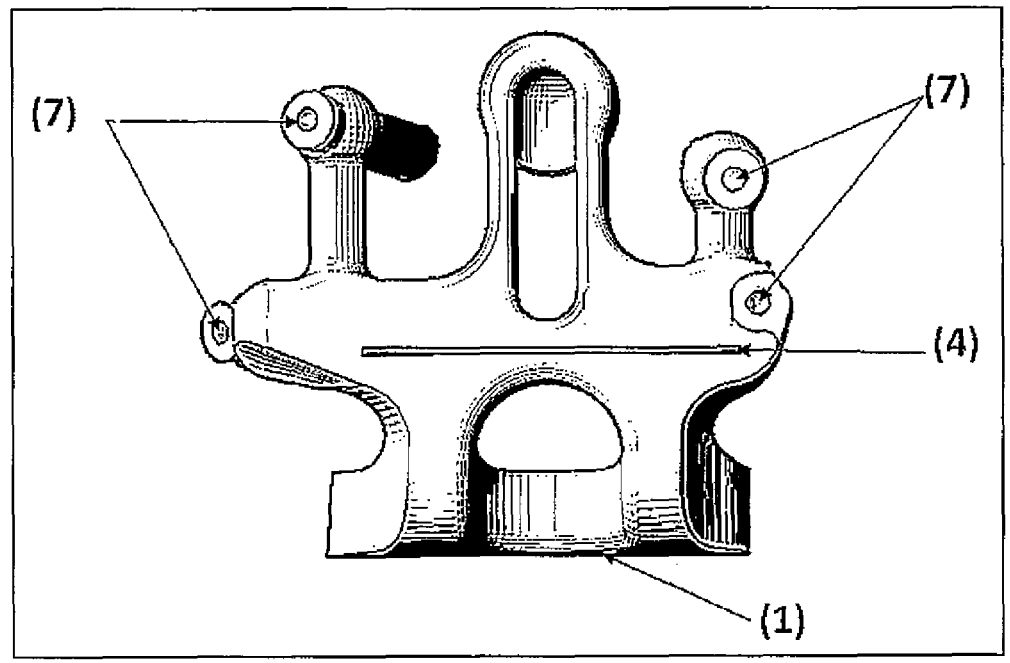
Figure 1-B Femoral template, top view

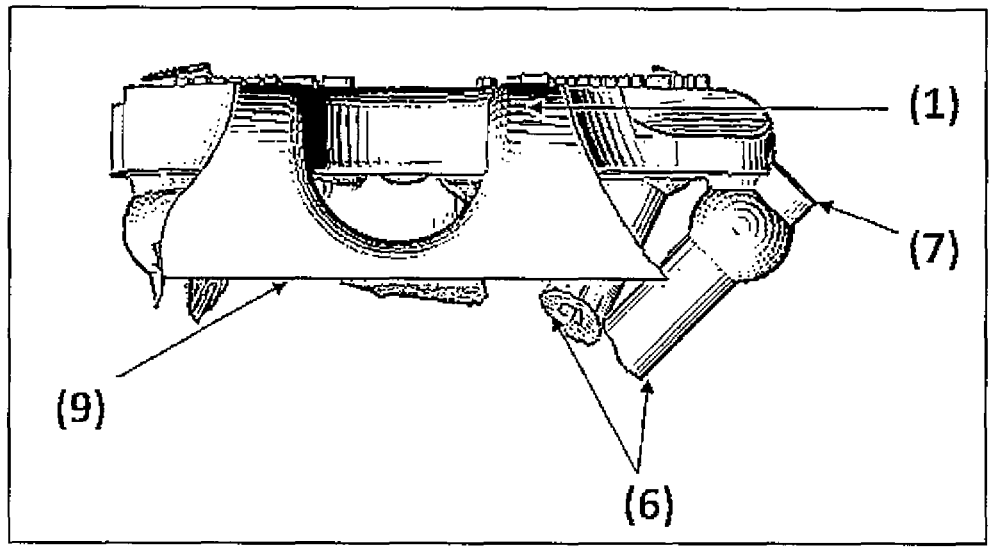
Figure 1-C Femoral template, front view
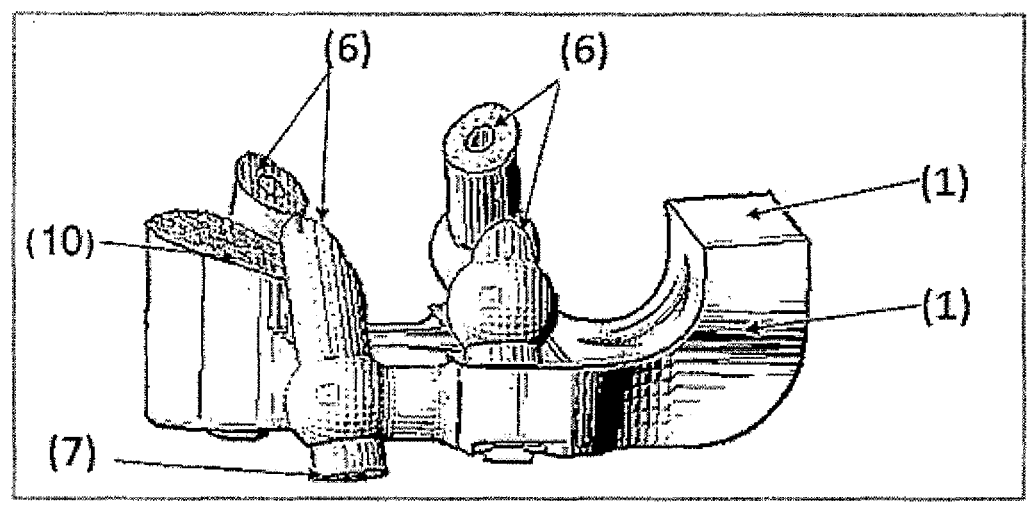
Figure 1-D Femoral template, side view

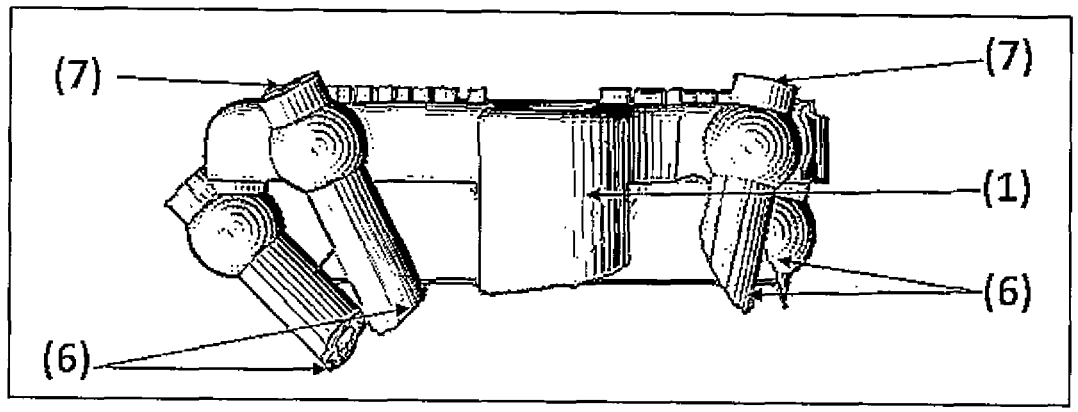
Figure 1-E Femoral template, Back view
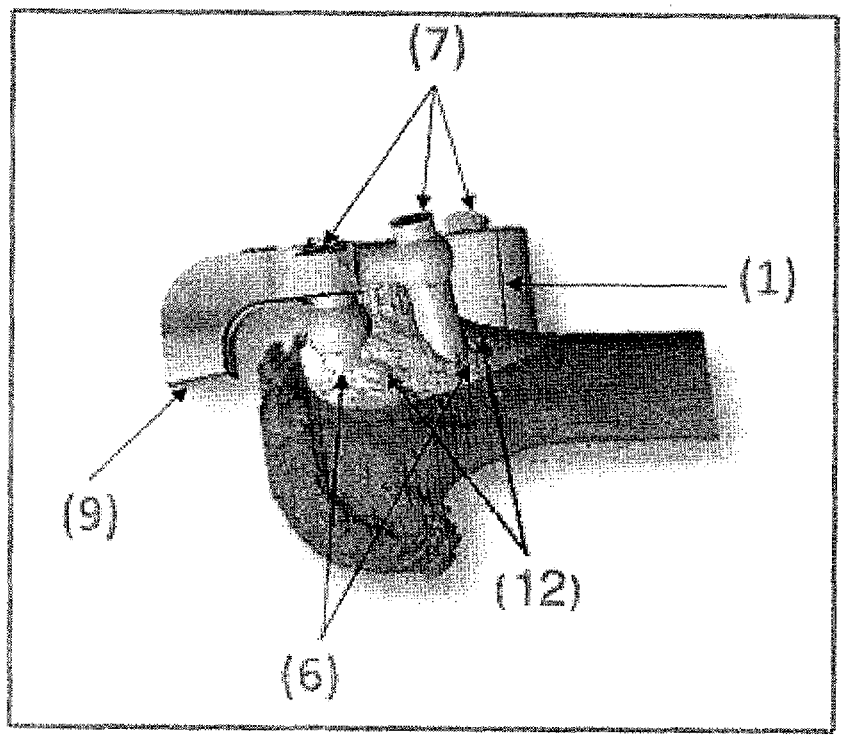
Figure 1-F Femoral template on a bone model (distal femur), side view

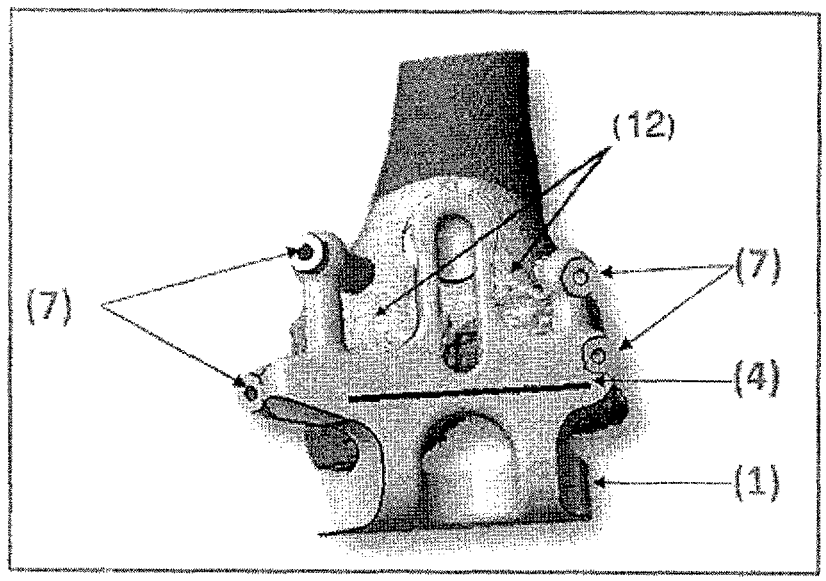
Figure 1-G Femoral template on a bone model (distal femur), top view
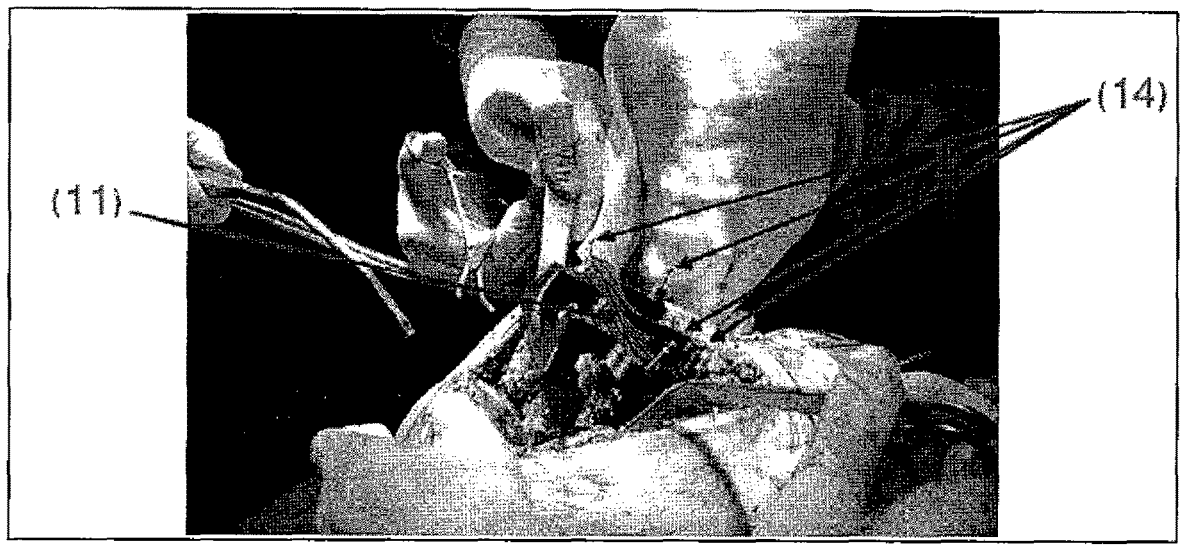
Figure 1-H Femoral template on a patient (distal femur), oblique view shows the top, the front and the side views while the template is fixed by pins

Figure 2 Tibial template
All views ( 2-A, 2-B, 2-C, 2-D, 2-E, 2-F, 2-G, 2-H, 2-I )
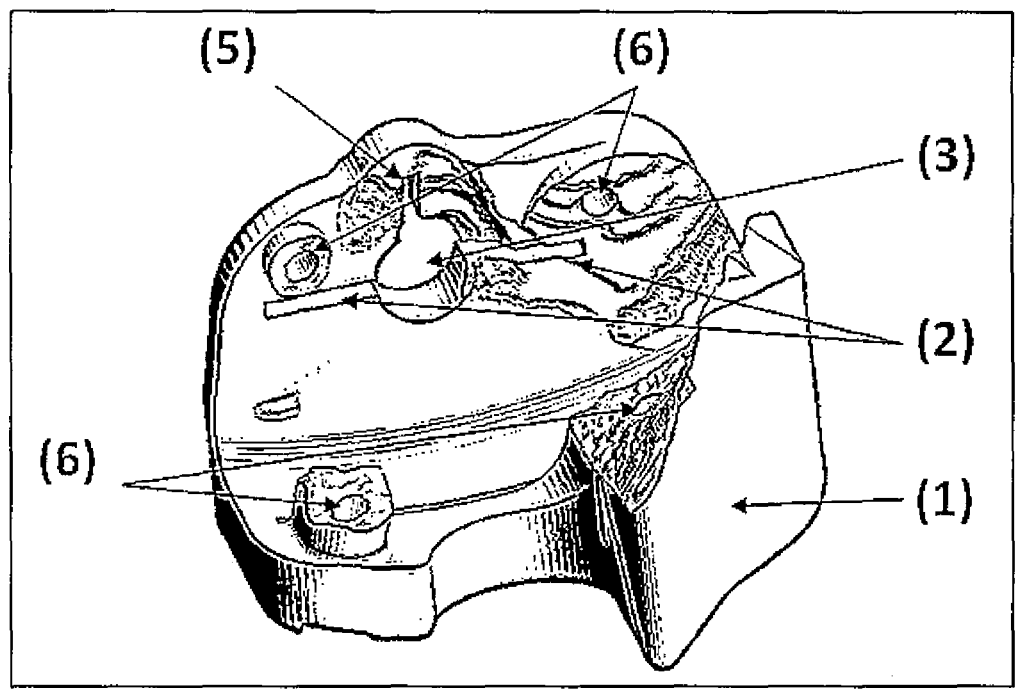
Figure 2-A Tibial template, inside view

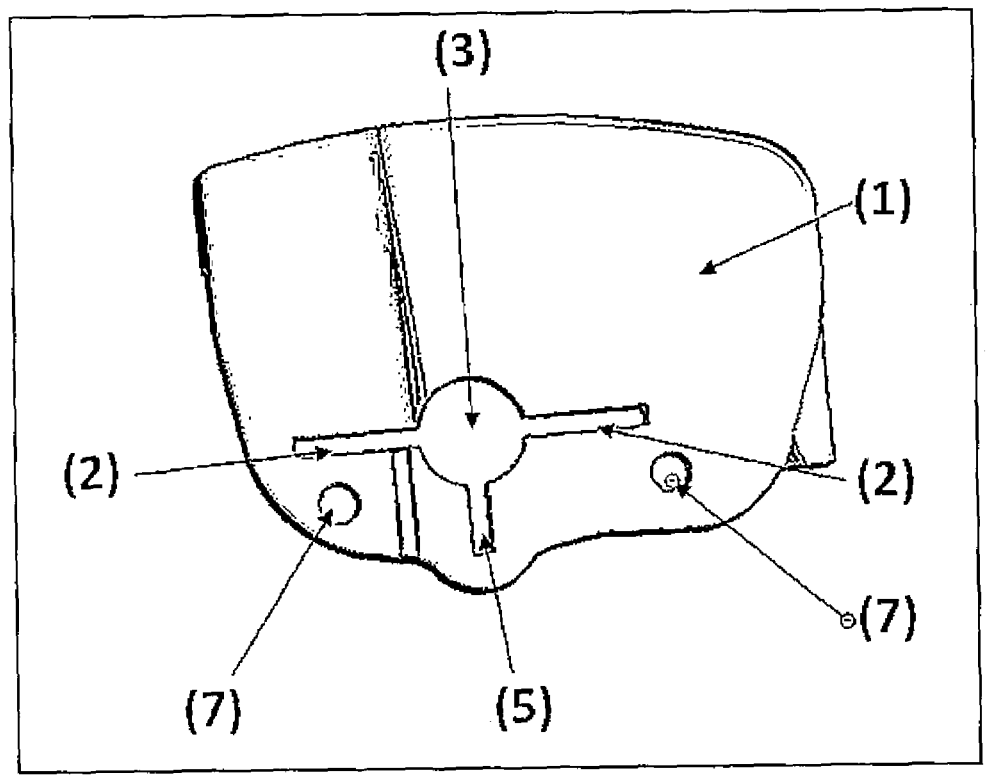
Figure 2-B Tibial template, top view
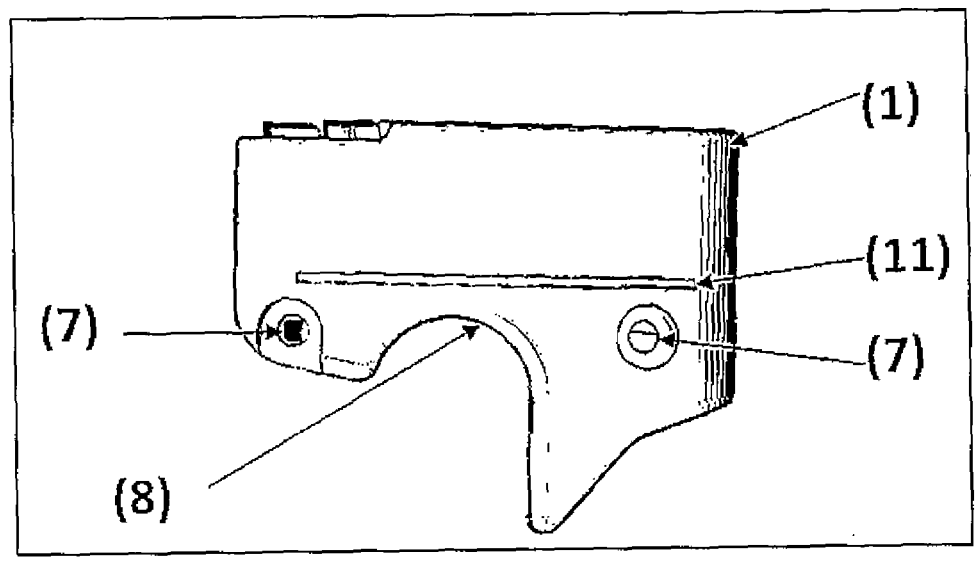
Figure 2-C Tibial template, front view

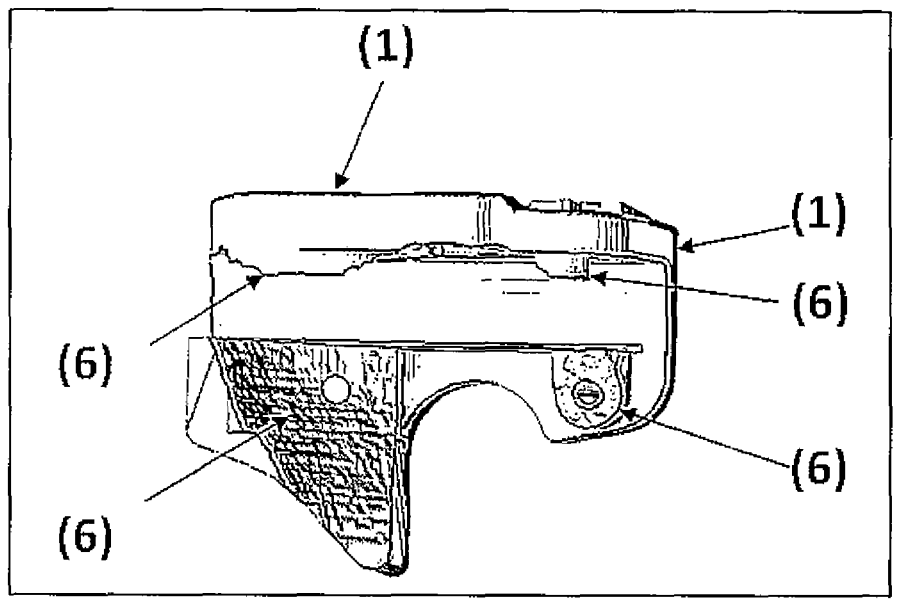
Figure 2-D Tibial template, back view
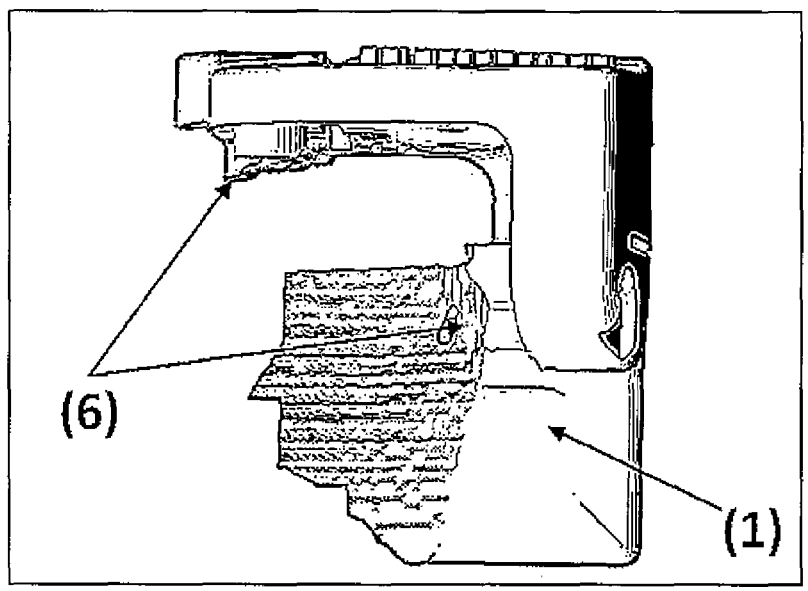
Figure 2-E Tibial template, side view-right

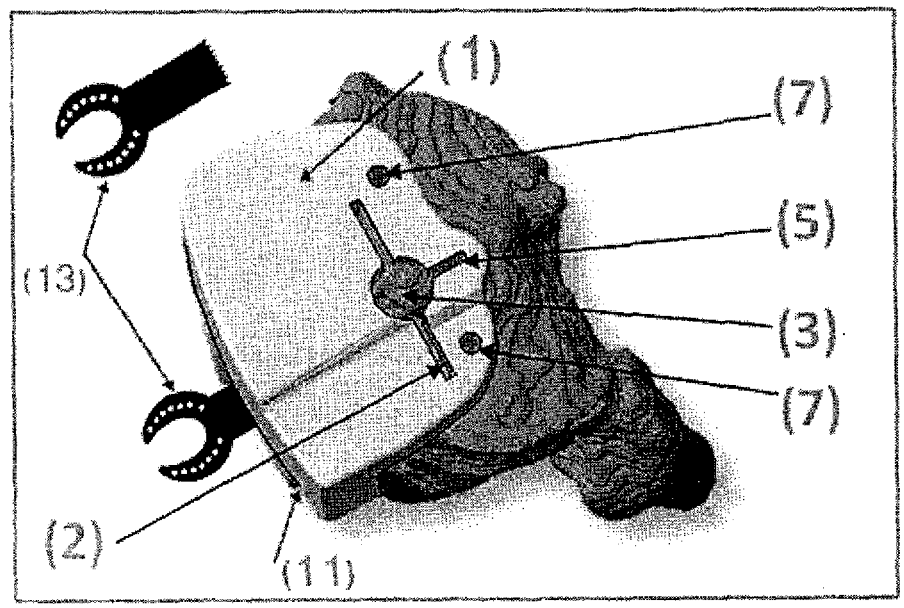
Figure 2-F Tibial template on a bone model, top view
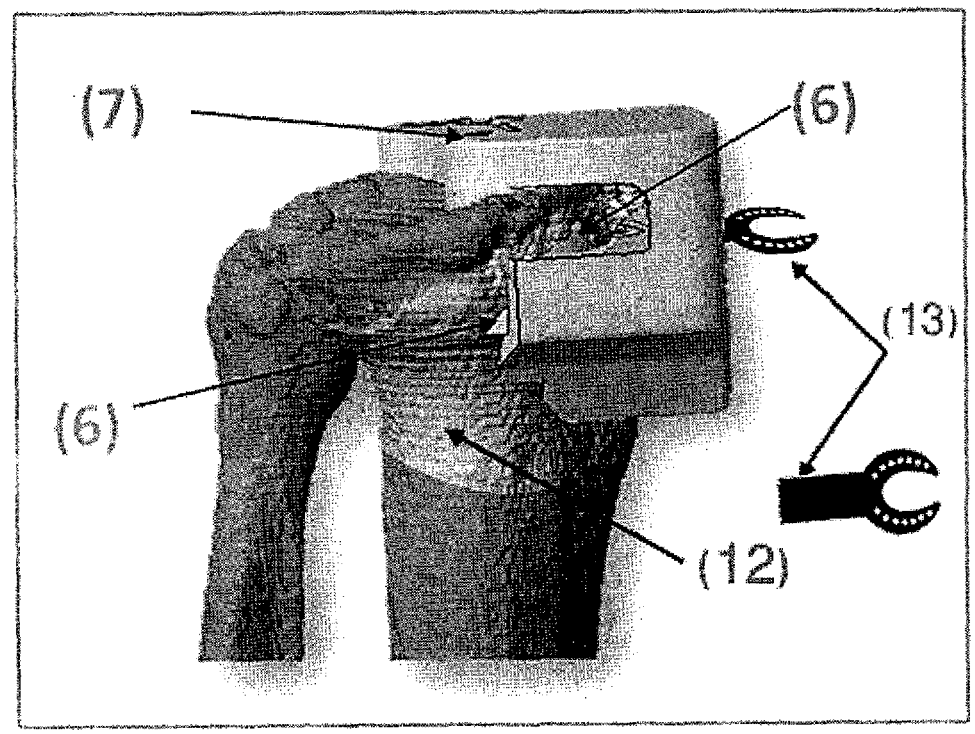
Figure 2-G Tibial template on a bone model, side view-left

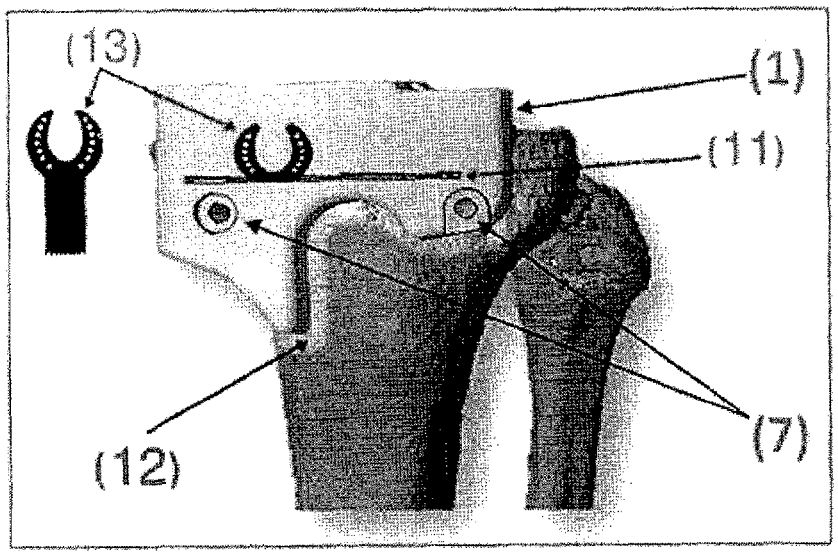
Figure 2-H Tibial template on a bone model, front view
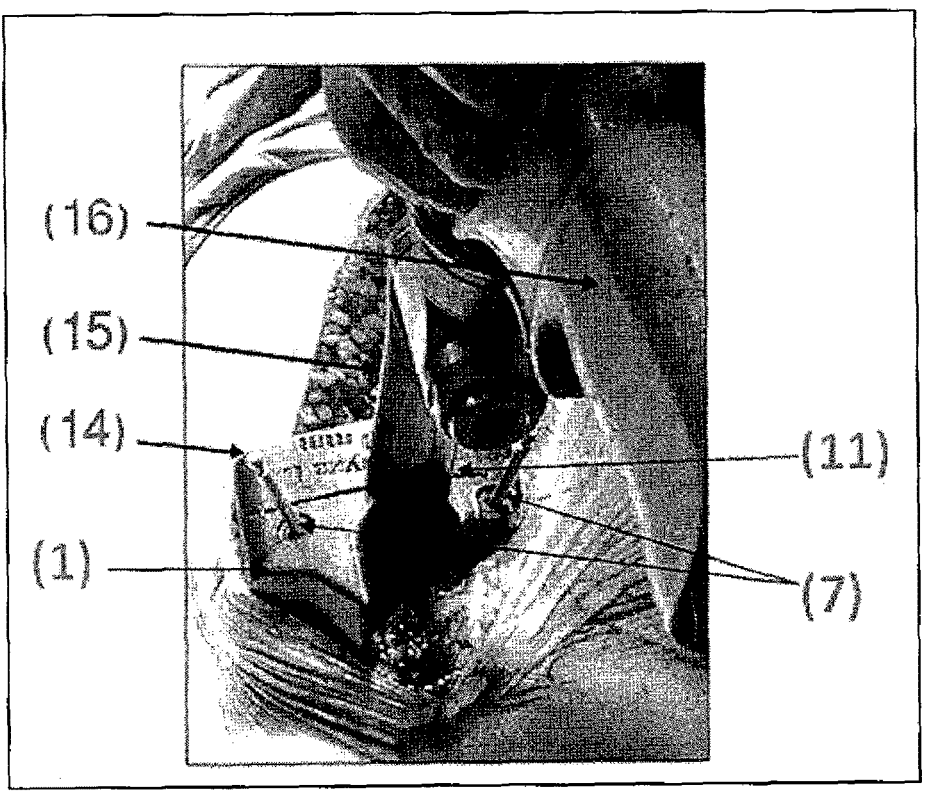
Figure 2-I Tibial template on a patient, front view with the saw blade inside the slit ready to cut the bone

DEVICE AND METHOD FOR FITTING AN ARTIFICIAL KNEE JOINT USING UNIVERSAL ELECTRONIC TEMPLATES WHICH CAN BE ADAPTED TO ALL ARTIFICIAL JOINTS

TECHNICAL FIELD

Total knee arthroplasty (TKA) is the standard treatment for advanced knee osteoarthritis. The aim of a TKA surgery is to achieve long-term implant survival and successful functional outcome with cost effectiveness and minimal complications. The success of a TKA is dependent on surgical techniques that require a high degree of accuracy and reproducibility. Technical errors can have detrimental effects on function and survival. Component malpositioning may lead to wear and loosening, or patellar instability which results in early failure and revision surgery. Current surgical techniques rely on plain radiographs for preoperative planning and standardized conventional instrumentation for performing the procedure. Plain radiographs have limited accuracy. Conventional instrumentations have been reported to have limitations that affect the ultimate accuracy of surgery, especially bone cutting and implant alignment. Conventional instrumentations are complex tools with numerous jigs and fixtures. Their assembly is time consuming and may lead to errors. Their repeated use carries a theoretical risk of contamination. The use of alignment guides involves violating the IM canal. This can lead to a greater risk of bleeding, infection, fat embolism, and fractures. Each knee prosthesis has its own instrumentation. In the United Kingdom, there are more than 30 knee prostheses, and it is not unusual to have different prostheses used by different surgeons in the same department. This may overload hospital inventory, sterilization services, nurses' learning curves, and operating room time. Although conventional surgical instrumentations have been refined, additional technologic improvements have been limited. Computer-assisted navigation and robotic techniques have proved to be more accurate than conventional instrumentations. However, the broad application of such techniques is limited by cost, complexity, set-up time, and long learning curve. Recently, a new technique was introduced to overcome the listed drawbacks. This technique called "Patient Specific Instruments for knee arthroplasty", which is a new concept of utilizing computer-assisted preoperative planning to provide custom made surgical guides that can partly or completely replace conventional instrumentation systems. This new technique of patient specific instruments (PSI) was first reported by Hafez et all-3

BACKGROUND ART

Patient Specific Instruments (PSI) for knee arthroplasty involves image-based preoperative planning, followed by the production of templates that match the surface geometry of the patient's bony structures. The templates are designed to transfer the preoperative planning to the intraoperative performance. The production machines range from computer numeric-controlled (CNC) to a more sophisticated technology of rapid prototyping (RP) which acts as a three-dimensional printer to produce physical objects from the three-dimensional computer-aided designs (virtual templates). A preoperative CT or MRI scan is imported to a special software system that has three-dimensional data of TKA implants to be used. Planning and virtual surgery is performed on the computer before it is done on real patients. This includes sizing, alignment, bone cutting and verification of optimal implantation and positioning. Two virtual templates are designed and transformed into surgical guides using rapid prototyping technology. Information built into these guides make them patient specific and can be used by surgeons as cutting guides or cutting blocks. Therefore, TKA can be done without using conventional intra or extramedullary guides. This revolutionary technique has potential advantages over conventional systems as it improves short term recovery, reduces operative time and the risk of bleeding and fat embolism as well as maintaining accuracy. It is particularly useful for cases of extra-articular deformities, especially in elderly patients. It is a midway between conventional techniques and other more complex computer assisted system such as navigation and robotics.

Problems with the Current Art:

The PSI technique is now produced by some implant companies manufacturing knee or other joint prostheses. The planning process and PSI for each company is based on the implant of that producing company; which implies that the PSI of one company cannot be used for the implant of another company 4-6. Thus, these PSI's are company specific and they are very expensive, which is a significant disadvantage since this limits the wide spread application of current availability of PSI. Furthermore, there are manufactured implants used by many surgeons around the world that does not have PSI, which deprives patients of the privilege of PSI. In addition, a serious limitation of current PSI technique is that the planning is done by technicians not by the surgeon, himself and the whole process in under the control of the implant company. Although the final planning may be made available for surgeons to review, surgeons are not in control of the planning. For this reason PSI technique is used for the straight forward knee replacement and not for complex cases of either intra-articular or extra-articular deformity.

REFERENCES

1. Hafez M A, Chelule K, et al. Computer assisted total knee replacement: Could a two-piece custom template replace the complex conventional instrumentations? Computer Aided Surgery. 2004; 9(3):93-4
2. Hafez M A, Jaramaz B, et al. Computer Assisted Surgery of the Knee: An overview. In Surgery of the Knee (4th Ed.). Install J N, Scott N (Eds). Philadelphia, Churchill Livingston. 2006, 1655-1674
3. Hafez M A, Chelule K, Seedhom B B, Sherman K P. Computer-assisted total knee arthroplasty using patient-specific templating. Clinical Orthopaedic and Related Research. 2006; 444:184-192
4. US 20120290272 A1 (Jason A. Bryan [US]) 15 Nov. 2012 (15/11/2012/11).
5. US 20110071533 A1 (Biomet Manufacturing Corp [US]) 24 March 201 (24/3/2011).
6. WO 2012154407 A2 (Smith & Nephew, Inc.) 15 Nov. 2012 (15/11/2012).

SUMMARY

A device for preparing a knee joint for a prosthesis in a patient undergoing total knee arthroplasty (TKA) surgery for any knee implant (prosthesis) in a universal and open platform fashion is proposed. The device comprises two parts: a femoral part and a tibial part. Both parts are designed in the form of cutting blocks that have locating probes, slits and a surface for bone cutting, guide for adjusting rotation and holes for pin fixation. The tibial part has a hole for the creation of the stem and a slit for the creation of the keel.

A method of planning and complete virtual surgery of TKR in a universal and an open platform technique leading to the production of the device mentioned in claim 1 is also proposed. This method comprises several steps including: sizing of implants, alignment, bone cutting and positioning of implants (prosthetic components) as well as virtual surgery.

The device may be suitable to be used for any currently available knee implants (all on-shelf implants) regardless of different shapes and configurations of these implants. The device may be used for all patient specific implants. The femoral part and the tibial part may be independent of the design of knee implants and can work universally with all different designs of implants.

The device may include locating probes that are cannulated and have optional metallic sleeves to allow fixation pins to pass through and securely fix the instrument to the bone. The device may be designed in the form of a cutting block, through which most of the bone machining steps are carried out. The trajectories for the bone machining steps such as saw and drills in addition to the path for fixation pins are multidirectional but they are mathematically positioned to prevent any intersection. The surface matching of the device may rely on protruding locating probes that match bony surfaces away from the cartilage i.e. positioned on a "cartilage free area"

The device may have one protruding removable probe for the femur that is positioned on a cartilage free area. The device may be positioned directly to the bone with no other interfaces (guides, sleeves or cutting blocks). The device may be suitable for any knee implants that could be produced in the future regardless of the design or the shape of knee implants.

The method may be suitable to be used for any commercially and currently available knee implant (on-shelf implants), as well as patient specific knee implants. The method may be suitable to be used for any knee implants that could be produced in future regardless of the design or shape of knee implants.

The method may include 3-D evaluation of the anatomy and pathology of the knee joint and identification of landmarks and axis followed by complete planning, including sizing of implants, alignment, bone cutting and positioning of the implants (prosthetic components) in a universal and an open platform technique. The method may include simulation of surgery and template designing in a universal and an open platform technique. The method may lead to the production of the device in claim 1 (instruments) that guide the bone cuts or guide the accurate positioning of the conventional cutting jigs to be used for all implants in an open platform technique (universal)

The method may comprise image-based 3-D preoperative planning to design the virtual templates which are then converted to physical templates using additive manufacturing such as rapid prototyping techniques. The method may involve planning for the whole TKA surgery including sizing, alignment and rotation with simulation of the virtual surgical result. The method does not require preoperative coupling with other surgical instruments such as drills or sleeves that are related to a particular company The plan may be transferred to a two piece instrument that can replace the conventional instrumentation for TKA such as intramedullary, extra-medullary guides, sizing, rotation guides. The method may be independent of the design of knee implants and can work universally with all different designs of implants.

BRIEF DESCRIPTION OF THE DRAWINGS

FIG. 1 illustrates a femoral template;
FIG. 1A illustrates an inside view of a femoral template;
FIG. 1B illustrates a top view of a femoral template;
FIG. 1C illustrates a front view of a femoral template;
FIG. 1D illustrates a side view of a femoral template;
FIG. 1E illustrates a rear view of a femoral template;
FIG. 1F illustrates a side view of a femoral template on a bone model;
FIG. 1G illustrates a top view of a femoral template on a bone model;
FIG. 1H illustrates a femoral template on a patient;
FIG. 2 illustrate a tibial plate. illustrates a tibial template;
FIG. 2A illustrates an inside view of a tibial template;
FIG. 2B illustrates a top view of a tibial template;
FIG. 2C illustrates a front view of a tibial template;
FIG. 2D illustrates a rear view of a tibial template;
FIG. 2E illustrates a right side view of a tibial template;
FIG. 2F illustrates a top view of a tibial template on a bone model;
FIG. 2G illustrates a left side view of a tibial template on a bone model;
FIG. 2H illustrates a front view of a tibial template on a bone model;
FIG. 2I illustrates a tibial template on a patient;
FIG. 3A demonstrates the use of the reference cut across a multitude of femoral implants;
FIG. 3B shows the distal femoral cut, the anterior femoral cut, and the proximal tibial cut; and
FIGS. 3C-3D show the data of different implants including all sizes of femoral and tibial components.

DETAILED DESCRIPTION

The invention is a device and a method for preparing a knee joint for a prosthesis in a patient undergoing TKA surgery for any knee implant (prosthesis) in a universal and an open platform fashion. The universal device and an open platform and method are suitable to be used for any commercially and currently available knee implant. The device and the method are used for all on-shelf implants and all patient specific implants. The universal and an open platform device and method are suitable to be used for any on-shelf and any patient specific knee implants that could be produced in future.

The device is a patient specific instrument, which is based on a method comprising of image based (CT, MRI or computed X-ray) 3-D preoperative planning to design the virtual templates, which are then converted to physical templates using computer aided manufacturing such as computer numerical control (CNC) or additive manufacturing such as rapid prototyping technologies. A method of planning and complete virtual surgery of TKA, which includes several steps; 3-D reconstruction and segmentation of computed tomography (CT) or MRI scan data. The preoperative planning that is comprised of 3-D evaluation of the anatomy and pathology of the knee joint and identification of landmarks and axes followed by complete planning including sizing alignment, bone cutting and positioning of implants (prosthetic components) followed by simulation of surgery and template designing. That method led to the production of the templates (instruments). One femoral and one tibial template were designed in the form of cutting blocks to allow bone preparation based on preoperative planning. This was achieved by creating slits (4) and (11) (shown FIGS. 1-G, 2-H) in the templates to allow bone cuts in the distal femur and the proximal tibia. As shown in FIGS. 1-A through 1-G, the template was designed to have five cylindrical locating probes (6) for the femur and four for the tibia (6) as shown in FIGS. 2-A, 2-D and 2-E. The template was designed to have five cylindrical locators for the femur and four for the tibia. These locators were created in the internal surfaces of the templates, matching the surface shape of the distal femur and proximal tibia. Because these locators were patient-specific, they could only allow the templates to be placed in a unique and secure position. The locators (6) were cannulated (7) to allow passage of the fixation pins (7) that provided additional stability to the templates over the bone as shown in FIGS. 1-A, 1-B and 1-D. As Shown in FIGS. 1-A and 1-B the femoral template is meant to allow the surgeon to perform the distal cut through the specified slit in the anterior face (4) and also guide the surgeon to mark the distal femur for the position, direction and angle of the anterior cut by using the end surface (9) to support the cutting saw as shown in FIGS. 1-A, 1-C, 1-D, 1-F. The previously mentioned cuts, in addition to one tibial cut, are referred to as the reference cuts which are planned independent of the brand or the size of the implant. Then a conventional cutting guide is used to make the remaining 3 cuts of the femur (posterior, anterior chamfer and posterior chamfer cuts). As shown in the FIGS. 2-A, 2-B and 2-F the Upper part of the tibial part has a drilling hole (3) for drilling the bone for the installation of stem and it has slits (2) and (5) to indicate the direction of tibial rotation and guide the position of the stem and keel if needed. There is a projection in the front of the lower part of tibial template to allow the attachment of a rod that goes down to the ankle as a double check for tibial rotation. Surgical simulation of bone cutting and implant positioning were performed using virtual templates. The final design of the custom templates (patient-specific instruments) was transferred electronically to a rapid prototyping machine. Patient-specific instruments then were produced from a material that is biocompatible and durable. Once manufactured, the templates were sterilized and used by the surgeon to perform TKA.

The device is specifically designed for TKA and the planning is based on a universal TKA prosthesis. The device has 2 parts; a femoral part and a tibial part both of them are independent of any commercially available knee implants and can work universally with all currently available implants or any implants introduced in future. The device has locating probes that are cannulated and have optional metallic sleeves to allow fixation pins to pass through and securely fix the instrument to the bone. The method involves planning for the whole TKA surgery including sizing, alignment and rotation with simulation of the virtual surgical result. No need for preoperative coupling with other surgical instruments such as drills or sleeves that are related to a particular company. The preoperative plan is transferred to a two piece instrument that can replace the conventional instrumentation for TKA such as intramedullary, extramedullary guides, sizing, rotation guides for both tibial and femur. The instrument is designed in the form of a cutting block, through which most of bone machining steps are carried out. The paths for the bone machining steps mentioned in claim 10 such as saw and drills in addition to the path for fixation pins are multidirectional but they are accurately positioned to prevent any interference between the fixation points and the cutting instruments. They are mutually changeable according to the anatomy of the knee joint as well as for each brand or design of the knee implant. As shown in FIGS. 1-A, 1-C, 1-D and 1-E, the surface matching of the templates relies on the essential protruding locating probes (6) where their ends match the bony surfaces away from the cartilage i.e. positioned on a "cartilage free area" in the distal femur and the proximal tibia. As shown in FIGS. 1-A, there is one protruding probe (10) for the femur that is positioned on a cartilage free area on the femoral trochlea, this probe is considered as an accessory part which can be removed. The device is an instrument (tool) not just a template. The instrument is positioned directly to the bone with no other interfaces (guides, sleeves or cutting blocks).

The same technique can be applied for other knee procedures such as unicompartmental, bicondylar and patellofemoral arthroplasty.

FIG. 1 has several views of the femoral template from (1-A to 1-H).

The template was designed to have five cylindrical locators for the femur (labels 6 and 10 in FIGS. 1-A, 1-D and 1-E). These locators were created in the internal surfaces of the templates, matching the surface shape of the distal femur. Because these locators were patient-specific, they could only allow the templates to be placed in a unique and secure position (FIGS. 1-F and 1-G). The locators were cannulated to allow passage of the fixation pins that provided additional stability to the templates over the bone (label 7 in FIGS. 1-F and 1-G). The femoral template is meant to allow the surgeon to perform the distal cut through the specified slit (label 4 in FIG. 1-B). The template also guides the surgeon to mark the distal femur for the position of and direction of anterior cut and rotation at the margin (free end) of the template (FIGS. 1-C and 1-D).

FIG. 2 has several views of the tibial template from 2-A to 2-I.

The template was designed to have four locators for the tibia as indicated by label 6 in FIG. 2. These locators were created in the internal surfaces of the templates (FIGS. 2-A, 2-D and 2-E), matching the surface shape of the proximal tibia (FIGS. 2-F, 2-G and 2-H). Because these locators were patient-specific, they could only allow the templates to be placed in a unique and secure position (FIGS. 2-F, 2-G and 2-H). The locators were cannulated to allow passage of the fixation pins which provided additional stability to the templates over the bone (FIG. 2-I). A slit in the upper part of tibial template indicates the direction of tibial rotation and guides the position of the stem (label 3, FIG. 2-B) and keel (label 2, FIG. 2-B) if needed. Another slit in the front of the tibial template allows the attachment of a rod that goes down to the ankle as a double check for tibial rotation (label 5 in FIG. 2-B).

The invention claimed is:

1. A method of forming a template for preparing a knee joint associated with a femur bone and a tibia bone in a patient undergoing total knee arthroplasty (TKA), comprising:

using patient-specific information, forming a femoral part of the template and a tibial part of the template, the femoral part of the template and the tibial part of the template together adapted for use in preparing the femur bone and the tibia bone designed to correlate to any TKA prosthesis wherein the forming step further comprises:

based on preoperative imaging, providing the femoral part with a plurality of cannulated locating probes protruding from the femoral part, the plurality of cannulated locating probes being located on the femoral part to match with bony surfaces away from any cartilage of the knee joint, the plurality of cannulated locating probes being patient-specific to allow placement of the femoral part in a unique and secure position on the femur bone;

wherein the forming step comprises forming the plurality of cannulated locating probes on the femoral part comprising two first probes in a lateral side of the femoral part, two second probes in a medial side of the femoral part, and further including one middle probe located between the first and second probes when connected to the femoral part, the middle probe adapted to be removed from the femoral part.

2. The method of claim 1, comprising the steps of:

designing a virtual template using three-dimensional information obtained from images of the knee joint; and forming the femoral part and the tibial part of the template to conform with the virtual template.

3. The method of claim 1, wherein the forming step comprises providing the femoral part and the tibial part with cutting slits, a surface for bone cutting, alignment and rotation guides, and holes adapted to fix the part over a corresponding bone surface.

4. The method of claim 1, wherein the forming step comprises forming a cutting slit in each of the femoral part and the tibial part.

5. The method of claim 1, wherein the forming step comprises forming the tibial part with a hole for the creation of a stem in the tibia, slits for the creation of a keel in the tibia, and a projection in a front of a lower portion of the tibial part to allow for the attachment of a rod for extending down to an ankle to check on tibial rotation.

6. The method of claim 4, wherein the forming step comprises providing the cannulated locating probes protruding from internal surfaces of the femoral part, and further including the step of providing a plurality of cannulated locating probes protruding from internal surfaces of the tibial part, the cannulated locating probes allowing fixation pins to pass there through and securely fix the femoral part over the femur bone and the tibial part over the tibia bone, wherein the paths for the fixation pins created by the cannulated locating probes are positioned to prevent any intersection among the fixation pins 49-F with a saw cut made using the cutting slits in the femoral part and tibial part.

7. The method of claim 1, wherein the forming step comprises forming the femoral part so as to allow a surgeon to perform a distal cut in the femur bone through a distal cut slit and to mark the femur bone for an anterior cut for any implant to be used.

8. A method of forming a template for preparing a knee joint associated with a femur bone and a tibia bone in a patient undergoing total knee arthroplasty (TKA), comprising:

using patient-specific information, forming a femoral part of the template and a tibial part of the template, the femoral part of the template and the tibial part of the template together adapted for use in preparing the femur bone and the tibia bone, the femoral part including five locator projections protruding from an interior surface of the femoral part for engaging the femur bone, the five locator projections including one removable locator projection located intermediate of two lateral pairs of the remaining four locator projections, and the tibial part including four locator projections protruding from an interior surface of the tibial part for engaging the tibia bone, the locating projections all being patient-specific to allow placement of the femoral part in a unique and secure position on the femur bone and the tibial part in a unique and secure position on the tibia bone;

wherein the forming step comprises positioning the locating projections on the femoral part of the template and tibial part of the template to match bony surfaces on the femur bone and the tibia bone away from any cartilage to ensure surface matching.

9. The method of claim 8, wherein the forming step comprises forming the femoral part so that it allows a surgeon to perform a distal cut in the femur bone through a distal cut slit and to mark the femur bone for an anterior cut for any implant to be used.

10. The method of claim 8, wherein the five locator projections comprise two probes on a lateral side, two probes on a medial side, and one probe removable from the femoral part.

* * * * *

UNITED STATES PATENT AND TRADEMARK OFFICE
CERTIFICATE OF CORRECTION

PATENT NO. : 10,849,636 B2  
APPLICATION NO. : 14/964609  
DATED : December 1, 2020  
INVENTOR(S) : Mahmoud Alm El Din Hafez Page 1 of 1

It is certified that error appears in the above-identified patent and that said Letters Patent is hereby corrected as shown below:

Column 8, Claim 6, Line 1 – please delete "49-F"

Signed and Sealed this  
Ninth Day of February, 2021

Drew Hirshfeld  
*Performing the Functions and Duties of the*  
*Under Secretary of Commerce for Intellectual Property and*  
*Director of the United States Patent and Trademark Office*